US005824530A

United States Patent [19]
Kemper et al.

[11] Patent Number: 5,824,530
[45] Date of Patent: Oct. 20, 1998

[54] OVEREXPRESSION OF RECOMBINANT BACTERIOPHAGE T4 ENDONUCLEASE VII AND USES THEREOF

[75] Inventors: Börries Kemper, Köln; Stefan Golz, Essen; Rainer P. Birkenbihl, Köln, all of Germany

[73] Assignee: Variagenics, Inc., Cambridge, Mass.

[21] Appl. No.: 621,708

[22] Filed: Mar. 28, 1996

Related U.S. Application Data

[60] Provisional application No. 60/003,104 Sep. 1, 1995.
[51] Int. Cl.$^6$ .................................................. C12N 9/22
[52] U.S. Cl. .............................................................. 435/199
[58] Field of Search .................................... 435/199, 975

[56] References Cited

U.S. PATENT DOCUMENTS 5,459,039  10/1995  Modrich et al. ............................. 495/6

OTHER PUBLICATIONS

Babon et al., Nucl. Acids Res. 23:5082–5084, 1995.
Barry et al., J. Biol. Chem. 269:33049–33062, 1994.
Barth et al., Genetics 120:329–343, 1988.
Benson et al., EMBO J. 13:5764–5771, 1994.
Bertrand–Burggraf et al., Mutation Research DNA Repair 314:287–295, 1994.
Bhattacharyya et al., J. Mol. Biol. 221:1191–1207, 1991.
Birkenbihl et al., J. Biol. Chem. 270:7703–771, 1995.
Birkenkamp and Kemper, DNA Res. 2:9–14, 1995.
Bradford, Anal. Biochem. 72:248–254, 1976.
Cazaux et al., Biol. Chem. 269:8246–8254, 1994.
Chi et al., J. Biol. Chem. 269:29984–29992, 1994.
Duckett et al., Cell 55:79–89, 1988.
Dunderdale et al., J. Biol. Chem. 269:5187–5194, 1994.
Flemming et al., Virology 196:910–913, 1993.
Frankel et al., J. Mol. Biol. 62:439–463, 1971.
Fujisawa and Minagawa, Virology 45:289–291, 1971.
Grebenshchikova et al., Genetika 30:622–626, 1994.
Jensch et al., EMBO J. 8:4325–4334, 1989.
Jensch and Kemper, EMBO J. 5:181–189, 1986.
Kemper and Brown, J. Virol. 18:1000–1015, 1976.
Kemper and Janz, J. Virol. 18:992–999, 1976.
Kemper et al., Eur. J. Biochem. 115:133–141, 1981.
Kemper and Garabett, Eur. J. Biochem. 115:123–131, 1981.
Kemper et al., Cold Spring Harbor Symp. Quant. Biol. 49:815–825, 1984.
Kemper et al., vol. 1:Human Genome Initiative & DNA Recombination (Sarma, R.H., Sarma, M.H. ed.) pp. 215–229, Adenine Press, Schenectady, NY, 1990.
Kleff and Kemper, EMBO J. 7:1527–1535, 1988.
Kosak and Kemper, Eur. J. Bichem. 194:779–784, 1990.
Laemmli, Nature 227:680–685, 1970.
Lilley and Kemper, Cell 36:413–422, 1984.
Minagawa and Ryo, Virology 91:222–233, 1978.
Minagawa and Ryo, Mol. Gen. Genet. 170:113, 1979.
Miyazaki et al., Genetics 104:1–9, 1983.
Mizuuchi et al., Cell 29:357–365, 1982.
Mosig et al., Cold Spring Harbor Symp. Quant. Biol. 49:371–382, 1984.
Mosig, Annu. Rev. Genet. 21:347–371, 1987.
Mueller et al., J. Biol. Chem. 265:13918–13924, 1990.
Murchie and Lilley, J. Mol. Biol. 233:77–85, 1993.
Pottmeyer and Kemper, J. Mol. Biol. 223:607–615, 1992.
Solaro et al., J. Mol. Biol. 230:868–877, 1993.
Studier et al., Methods in Enzymology, vol. 185 (Goeddel, D.V. ed.) pp. 60–89, Academic Press, Inc. San Diego, 1991.
Wilson et al., Nature 280:80–81, 1979.
Youil et al., Proc. Natl. Acad. Sci. USA 92:87–91, 1995.
Giraud–Panis, M., et al. (1995) J. Mol. Biol. 252, 596–610.
Golz, S., et al. (1995) DNA Res. 2, 277–284.
Golz et al., Chem. abstr. vol. 124, No. 17, p. 1249, abstract No. 230075m (1996).

*Primary Examiner*—Charles L. Patterson, Jr.
*Attorney, Agent, or Firm*—Clark & Elbing LLP

[57] ABSTRACT

Disclosed are improved methods for the production and recovery of bacteriophage T4 endonclease VII.

19 Claims, 3 Drawing Sheets

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 39
        ( B ) TYPE: nucleic acid ( C ) STRANDEDNESS: single
( D ) TOPOLOGY: linear ( x i ) SEQUENCE DESCRIPTION: SEQ ID NO: 1:

GGGCTCGAGG CCTTAATGTT ATTGACTGGC AAATTATAC        39

( 2 ) INFORMATION FOR SEQ ID NO: 2:

( i ) SEQUENCE CHARACTERISTICS:
( A ) LENGTH: 35
( B ) TYPE: nucleic acid
( C ) STRANDEDNESS: single
( D ) TOPOLOGY: linear ( x i ) SEQUENCE DESCRIPTION: SEQ ID NO: 2:

ATGAATTAAG ATCTCAATTT CTTTTTCAAT TGTCA        35

( 2 ) INFORMATION FOR SEQ ID NO: 3:

( i ) SEQUENCE CHARACTERISTICS:
( A ) LENGTH: 27
( B ) TYPE: nucleic acid
( C ) STRANDEDNESS: single
( D ) TOPOLOGY: linear ( x i ) SEQUENCE DESCRIPTION: SEQ ID NO: 3:

TCAAAGAATT CCGGATTAGG GATCCCC        27

( 2 ) INFORMATION FOR SEQ ID NO: 4:

( i ) SEQUENCE CHARACTERISTICS:
( A ) LENGTH: 28
( B ) TYPE: nucleic acid
( C ) STRANDEDNESS: single
( D ) TOPOLOGY: linear ( x i ) SEQUENCE DESCRIPTION: SEQ ID NO: 4:

AGGGGATCCC TAAGCTCCAT CGATGTAG        28

( 2 ) INFORMATION FOR SEQ ID NO: 5:

( i ) SEQUENCE CHARACTERISTICS:
( A ) LENGTH: 26
( B ) TYPE: nucleic acid
( C ) STRANDEDNESS: single
( D ) TOPOLOGY: linear ( x i ) SEQUENCE DESCRIPTION: SEQ ID NO: 5:

CTAGGCCTAG CGTCCGGAAT TCTTTG        26

( 2 ) INFORMATION FOR SEQ ID NO: 6:

( i ) SEQUENCE CHARACTERISTICS:
( A ) LENGTH: 27
( B ) TYPE: nucleic acid
( C ) STRANDEDNESS: single
( D ) TOPOLOGY: linear ( x i ) SEQUENCE DESCRIPTION: SEQ ID NO: 6:

GCTACATCGA TGGAGCCGCT AGGCCTA        27

( 2 ) INFORMATION FOR SEQ ID NO: 7:

( i ) SEQUENCE CHARACTERISTICS:
( A ) LENGTH: 46
( B ) TYPE: nucleic acid
( C ) STRANDEDNESS: single
( D ) TOPOLOGY: linear ( x i ) SEQUENCE DESCRIPTION: SEQ ID NO: 7:

GCCTCGAGGT CCGACTCTAG AGGCCTCTAG AGTCCGACCT CGAGGC    46

OVEREXPRESSION OF RECOMBINANT BACTERIOPHAGE T4 ENDONUCLEASE VII AND USES THEREOF

This application claims priority from provisional application Ser. No. 60/003,104, filed on Sep. 1, 1995. This invention relates to recombinant bacteriophage T4 endonuclease VII and improved methods for overexpressing and purifying this enzyme.

In vivo, bacteriophage T4 endonuclease VII ("T4 Endo VII") is a resolvase that is required for normal phage development. In addition, this enzyme has been reported to cleave very fast sedimenting DNA (VFS-DNA) and has been demonstrated to be involved in DNA-packaging, genetic recombination, and mismatch repair (Frankel et al., *J. Mol. Biol.* 62:439–463, 1971; Fujisawa et al., *Virology* 45:289–291, 1971; Kemper et al., *J. Virol.* 18:1000–1015, 1976; Kemper et al., *J. Virol.* 18:992–999, 1976; Minagawa et al., *Virology* 91:222–233, 1978; Minagawa et al., *Mol. Gen. Genet.* 170:113, 1979; Kemper et al., *Eur. J. Biochem.* 115:133–141, 1981; Kemper et al., *Eur. J. Biochem.* 115:123–131, 1981; Miyazaki et al., *Genetics* 104:1–9, 1983; Mosig et al., *Cold Spring Harbor Symp. Quant. Biol.* 49:371–382, 1984; Mosig, *Annu. Rev. Genet.* 21:347–371, 1987; Grebenshchikova et al., *Genetika* 30:622–626, 1994). Studies in vitro have revealed that purified T4 Endo VII specifically cleaves at secondary structures in double-stranded DNA. These structures include branched DNAs, four-way Holliday-structures, three-way Y-structures, single-strand overhangs, and even curved DNA (Kemper et al., *Cold Spring Harbor Symp. Quant. Biol.* 49:815–825, 1984; Mizuuchi et al., *Cell* 29:357–365, 1982; Duckett et al., *Cell* 55:79–89, 1988; Bhattacharyya et al., *J. Mol. Biol.* 221:1191–1207, 1991; Lilley et al., *Cell* 36:413–422, 1984; Jensch et al., *EMBO J.* 5:181–189, 1986; Kemper et al., *Structure & Methods* Vol. 1: *Human Genome Initiative & DNA Recombination*, eds., Sarma and Sarma, pp. 215–229, Adenine Press, Schenectady, N.Y., 1990; Pottmeyer et al., *J. Mol. Biol.* 223:607–615, 1992). Other reported substrates for T4 Endo VII include single base mispairings, heteroduplex loops (for example, loops arising from insertions, deletions, inversions, or transpositions), and bulky adducts (Kleff et al., *EMBO J.* 7:1527–1535, 1988; Solaro et al., *J. Mol. Biol.* 230:868–877, 1993; Birkenkamp et al., *DNA Res.* 2:9–14, 1995; Bertrand-Burggraf et al., *Mutations Research* 13:484–489, 1994; Murchie et al., *J. Mol. Biol.* 233:77–85, 1993).

Mechanistically, T4 Endo VII resolves DNA secondary structures, e.g., cruciform conformations, by introducing double-stranded breaks across the junction points, resulting in the incorporation of a limited number of closely staggered nicks in each 3' flanking region. The ability of T4 Endo VII to cleave precisely and non-processively at a variety of mismatches in double-stranded nucleic acid makes it an ideal reagent for mutation detection, for example, for the detection of mutations in eukaryotic genes (Youil et al., *Proc. Natl. Acad. Sci. USA* 92:87–91, 1995).

SUMMARY OF THE INVENTION

In general, the invention features an improved method for the production of bacteriophage T4 endonuclease VII (T4 Endo VII) that involves: (a) providing a host cell that includes a nucleic acid encoding T4 Endo VII, wherein expression of the T4 Endo VII is inducible; (b) inducing expression of the T4 Endo VII by applying a chemical stimulus; and (c) recovering the inducibly expressed T4 Endo VII from the host cell. Preferably, the host cell is a prokaryotic cell (e.g., an *E. coli* cell, for example, *E. coli* BL21(DE3)); the expression of T4 Endo VII is fully repressed prior to induction; the expression of T4 Endo VII is repressed by the lac repressor prior to induction; the expression of T4 Endo VII is under the control of a T7 promoter; T4 Endo VII is inducibly transcribed by T7 RNA polymerase; T4 Endo VII is inducibly expressed by treatment with the chemical stimulus IPTG; and the nucleic acid encoding T4 Endo VII is contained within a pET vector (e.g., the pET-11a vector).

In other preferred embodiments, the T4 Endo VII is recovered in a soluble form; recovery includes a heparin chromatography step; recovery includes a Mono-Q chromatography step; T4 Endo VII is produced in quantities of at least 0.4 mg/kg of host cells and, preferably, at least 0.5 mg/kg of host cells; and the recovered T4 Endo VII has a purity of at least 90% and, preferably, at least 99%.

In yet other preferred embodiments, the recovered T4 Endo VII has a specific activity of at least $5 \times 10^7$ U/mg, more preferably, at least $6 \times 10^7$ U/mg, and, most preferably, at least $2.5 \times 10^8$ U/mg.

In related aspects, the invention features recombinant T4 Endo VII produced according to the methods of the invention, and kits including this recombinant T4 Endo VII.

By "inducible" is meant that expression of the protein product is increased in response to a chemical stimulus. In one particular example described herein, induction of T4 Endo VII expression is provided indirectly by treatment with the chemical stimulus, isopropyl-1-thio-β-D-galactoside ("IPTG"). This chemical stimulus mediates the inducible expression of T7 RNA polymerase (i.e., the polymerase gene is under the control of the IPTG-inducible lacUV5 promoter). Upon induction, this polymerase facilitates expression of T4 Endo VII (which, in the system described herein, is under the control of the bacteriophage T7 promoter and translation signals). Examples of other regulatory regions useful for the inducible expression of T4 Endo VII include, without limitation, the arabinose, galactose, and alkaline phosphatase regulatory regions. Inducible expression may be direct (for example, the T4 Endo VII gene may be directly linked to the chemically induced regulatory region), or it may be indirect (for example, intermediate regulatory proteins or expression enzymes may be induced which then mediate expression of T4 Endo VII expression). The term "inducible" does not include increased protein production that results exclusively from alterations in a host cell culture temperature.

By "recovering" is meant obtaining, in this case, T4 Endo VII from the host cell by any means and in any amount.

By "fully repressed" is meant that a gene expression fails to produce a level of protein product which is measurable by standard Western blotting techniques.

By the "lac repressor" is meant any wild-type or mutant form of the *E. coli* lactose repressor which is capable of decreasing expression of a gene upon binding to that gene's regulatory region.

Unless otherwise defined, all technical terms and scientific terms used herein have the same meaning as commonly understood by one of ordinary skill in the art to which the invention belongs. All publications mentioned herein are incorporated by reference.

The invention described herein provides a number of important advantages for the production of T4 Endo VII protein. For example, the methods of the invention provide a simple and inexpensive means for inducibly overexpressing and recovering milligram quantities of T4 Endo VII. By and recovering milligram quantities of T4 Endo VII. By providing a heterologous expression system that tightly controls and coordinates T4 Endo VII expression, the method of the invention minimizes the digestion of host DNA associated with this enzyme's expression and allows for significantly higher production levels. Furthermore, overproduction of T4 Endo VII in a heterologous expression system simplifies recovery of the expressed enzyme. For example, as described herein, purification of bacteriophage T4 Endo VII of high specific activity is accomplished in as few as two chromatographic steps.

Other features and advantages of the invention will be apparent from the following detailed description and from the claims.

DETAILED DESCRIPTION

The drawings will first be described.

Drawings

FIGS. 1A and 1B are photographs demonstrating isopropyl-1-thio-β-D-galactoside ("IPTG")-inducible expression of recombinant wild-type and amE727-mutant T4 Endo VII resolvases. These proteins were produced in cultures of E. coli BL21(DE3) transformed with the plasmids pRB210 or pRB211, respectively, and protein production was analyzed by reducing SDS-PAGE (FIG. 1A) or Western Blot (FIG. 1B) techniques. Cultures were grown to an $OD_{550}$=0.8 and split, with one half of the culture being induced with IPTG and the other half left untreated. After two additional hours of growth at 30° C., 3 µl of each culture was removed for analysis. FIG. 1A shows a reducing SDS-PAGE profile of protein extracts obtained from different IPTG-induced (+) and uninduced (-) BL21(DE3) cultures; protein FIG. 1B shows a Western blot of the protein extracts of FIG. 1A (except that 0.1 ng of T4 Endo VII was loaded in the marker lane). This Western blot was probed with T4 Endo VII antiserum at a dilution of 1:5000. As designated at the top of the gels, protein extracts were prepared from IPTG-induced (+) or uninduced (-) BL21(DE3) cultures expressing either the pET-11a (control), pRB210, or pRB211 plasmids. Lanes marked "M" contained marker proteins, and those marked "E VII" contained purified T4 Endo VII. As shown, the mutant protein is smaller than the wild-type protein. The second band on the Western blot in lane 7 of FIG. 1B, migrating at 34 kD, resulted from incomplete protein reduction and resultant dimer formation.

FIG. 4A shows the complete nucleotide sequence and structural conformation of intermolecular pairings between complementary sequences of the cruciform Bea-CF01 substrate, which was assembled in vitro from four synthetic oligonucleotides which are boxed and numbered as 1–4. An asterisk (*) shown at the 5' end of Strand 4 designates the addition of $^{32}p$ by end-labelling. Arrows shown within Strand 4 point to sites which are cleaved by T4 Endo VII. Cleavage sites in the other strands are not shown. FIG. 4B is a 12% denaturing polyacrylamide gel showing the analysis of reaction product fragments resulting from the treatment of the cruciform Bea-CF01 substrate (2 fmol) with 0, 5, 10, or 20 units of E. coli BL21(DE3)-purified T4 Endo VII under the assay conditions described herein. The arrow shown at the left of the gel indicates the position of the major T4 Endo VII-induced cleavage fragment of the cruciform Bea-CF01 substrate. The units of E. coli BL21(DE3)-purified T4 Endo VII which were added to each reaction mixture are shown at the top of the gel. FIG. 4C shows the complete nucleotide sequence and conformation of intramolecular pairings between complementary sequences of the hairpin Bea-MMCC(H46) oligonucleotide substrate. The 46mer Bea-MMCC(H46) oligonucleotide was designed as a self-complementary synthetic hairpin with a C/C-mismatch. The asterisk (*) shown at the 5'-end of the Bea-MMCC (H46) oligonucleotide designates the addition of $^{32}p$ by end-labelling. The arrows point to sites cleaved by T4 Endo VII. FIG. 4D is a 12% denaturing polyacrylamide gel showing the analysis of reaction product fragments resulting from the treatment of the hairpin Bea-MMCC(46) substrate (2 fmol) with 0, 20, 40, or 80 units of E. coli BL21(DE3)-purified T4 Endo VII under the assay conditions described herein. The arrows shown at the left of the gel indicate the position of the T4 Endo VII-induced cleavage fragments of the Bea-MMCC(H46) oligonucleotide substrate.

FIG. 5 is a photograph of a 15% polyacrylamide gel showing the silver-stained SDS-PAGE analysis of T4 Endo VII at different stages of purification. T4 Endo VII was purified from IPTG-induced cells of E. coli BL21(DE3) transformed with plasmid pRB210 as described herein. Lane 1, marker protein (M); lane 2, 6 µg of protein from Fraction I (crude extract following ultracentrifugation); lane 3, 6 µg of protein from Fraction II (PEG/Dex two phase separation); lane 4, 4 µg of protein from Fraction III (eluate of the heparin-agarose chromatography); and lane 5, 4 µg of protein from Fraction IV (eluate of Mono-Q column chromatography). The position of the molecular mass standards and of purified T4 Endo VII (designated as "E VII") are shown at the left and right of the gel, respectively.

There now follow examples demonstrating the inducible expression and subsequent recovery of milligram quantities of T4 Endo VII. These examples are provided for the purpose of illustrating, not limiting, the invention.

Cloning Of T4 Gene 49 into Expression Vector pET-11a

To clone the wild-type and amE727-mutant T4 Endo VII enzymes, gene 49 and amE727-mutant gene 49 were amplified using either genomic T4 GT7 DNA (Wilson et al., Nature 280: 80–81, 1979) or GT7amE727 DNA (Flemming et al., Virology 196: 910–913, 1993) as a template, and standard polymerase chain reaction methods. The oligonucleotide PCR primers used for amplification were as follows:

Upstream Primer:
5'-GGGCTCGAGGCCTTAATGTTATTGACTGGCAAAT-TATAC-3'(SEQ ID NO:1);
Downstream Primer:
5'-ATGAATTAAGATCTCAATTTCTTTTTCAATTGTCA-3'(SEQ ID NO:2).

The underlined sequences designate regions of the primers which are homologous to the genomic region of T4 gene 49. Oligonucleotides were purchased from Eurogentec (Belgium) and were subsequently purified according to standard procedures (Kemper et al., In: *Structure & Methods Vol. 1: Human Genome Initiative & DNA Recombination*, Sarma and Sarma, eds., pp. 215–229, Adenine Press, Schenectady, N.Y., 1990; Pottmeyer et al., *J. Mol. Biol.* 223:607, 1992).

To construct the pET-11a expression vector, the amplified PCR products were digested with StuI and BglII and ligated into an NdeI/Klenow/BamHI-treated pET-11a vector downstream of the T7Φ10 promoter (Studier et al., *Meth. Enzymol.* 185: 60–89, 1991). The host cells into which this vector was transformed contained the T7 RNA polymerase gene under the control of the *E. coli* lac operator. pET-11a contained a constitutively expressed lac repressor gene, which in the uninduced state provided an excess of lac repressor to block expression of both the T7 RNA polymerase and the T4 Endo VII genes.

The resulting IPTG-inducible expression plasmids (containing either the wild-type gene 49 (pRB210) or the amE727-mutant gene 49 (pRB211)) were transformed into *E. coli* strain BL21(DE3) according to standard methods. The pRB211 plasmid encoded an inactive T4 Endo VII, lacking seven C-terminal amino acids (Barth et al., *Genetics* 120:329–343, 1988).

IPTG-Inducible Expression of T4 Endo VII and AmE727-Mutant T4 Endo VII

To examine the IPTG-inducible expression of T4 Endo VII, BL21(DE3) strains transformed with plasmids pET-11a, pRB210, or pRB211 were grown to $OD_{550}$=0.8 in LB (i.e., 10 g bacto tryptone (Difco, Detroit, Mich.), 5 g yeast extract (Difco), and 10 g NaCl) containing ampicillin (100 µg/ml) according to standard methods. The cultures were then split; one part was induced by adding IPTG to a final concentration of 1 mM, and the other part remained uninduced. Following two hours of growth at 30° C., 3 µl of each culture were removed, and protein extracts from both IPTG-induced and uninduced BL21(DE3) cultures were prepared according to standard methods. The resulting protein extracts were analyzed by reducing SDS-PAGE electrophoresis and Western blotting.

For SDS-PAGE analysis, the protein extracts were denatured in sample buffer (3X: 150 mM Tris/HCl (pH 6.8), 6 mM EDTA, 3% SDS (mass/vol.), 3% 2-mercaptoethanol (ME) (by vol.), 24% glycerol (by vol.), and 0.075% bromphenol-blue (mass/vol.)) and separated on a reducing SDS polyacrylamide gel by the method of Laemmli (*Nature* 227:680–685, 1970). Gels were subsequently stained with Coomassie blue according to Maniatis et al. (*Molecular Cloning: A Laboratory Manual*, Cold Spring Harbor Laboratory, Cold Spring Harbor, N.Y., 1982).

Figure 1A:
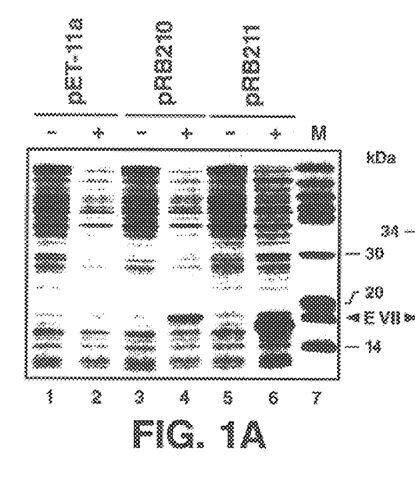

As shown in FIG. 1A, this analysis revealed the efficient expression of wild-type and mutant T4 Endo VII in the IPTG-induced BL21(DE3) cultures containing expression plasmids pRB210 and pRB211, respectively. No T4 Endo VII protein was detected in uninduced cultures. While wild-type T4 Endo VII was found to account for approximately 2% of the total protein extract prepared from *E. coli* BL21(DE3) expressing pRB210, approximately 50% of the total protein obtained from this strain expressing pRB211 was determined to be amE727-mutant T4 Endo VII. The difference in the expression of wild-type T4 Endo VII versus amE727-mutant T4 Endo VII was due to the fact that, upon induction, wild-type T4 Endo VII degrades intracellular DNA, including the gene encoding T4 Endo VII. Consequently, only a limited amount of wild-type T4 Endo VII RNA is available for translation. In contrast, mutant T4 Endo VII, which is unable to degrade host DNA, does not exhibit this characteristic reduction in protein expression. As shown in FIG. 1A, BL21(DE3) cultures expressing the pET-11a vector alone did not express T4 Endo VII under either induced or uninduced conditions.

Figure 1B:
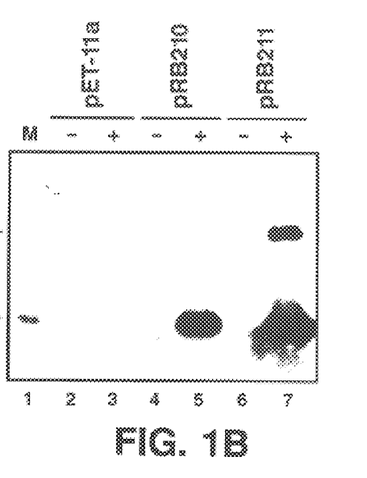

Western blot analyses of fractionated protein extracts prepared from IPTG-induced and uninduced cultures were performed as described in Birkenbihl and Subramani (*J. Biol. Chem.* 270: 7703–7711, 1995) using the ECL™ Western Blotting Detection System from Amersham (Braunschweig, Germany). Loading lanes with equal amounts of protein, it was found that the T4 Endo VII antiserum No. 64/3 described in Kosak et al.(*Eur. J. Biochem.* 194:779–784, 1990) and used at a 1:5000 dilution specifically detected the expression of both the wild-type and amE727-mutant T4 Endo VII enzymes in IPTG-induced cultures (FIG. 1B). T4 Endo VII protein was not detected in the uninduced cultures (FIG. 1B), nor was T4 Endo VII detected in cells expressing the control plasmid, pET11-a.

Activity of Recombinant Wild-Type and AmE727-Mutant T4 Endo VII In Crude Lysates To determine the activity of wild-type and amE727-mutant T4 Endo VII enzymes, crude lysates of BL21(DE3) cells expressing those proteins were prepared and tested for site-specific cleavage activity using a standard DNA cleavage assay and the plasmid substrate M13mp21IR62E (Jensch et al., *EMBO J.* 5:181–189, 1986; Mueller et al., *J. Biol. Chem.* 265:13918–13924, 1990). For these experiments, the phage M13mp21IR62E was engineered to contain a cruciform structure by inserting a perfect palindrome of 2×31 bp into the unique EcoRI restriction site, as described by Jensch et al. (*EMBO J.* 8:4325–4334, 1989). When supercoiled, the inserted palindromic inverted repeat of plasmid M13mp21IR62E adopts a cruciform configuration. T4 Endo VII cleaves specifically at the base of this cruciform structure, linearizing the plasmid. For localization and verification of T4 Endo VII cleavage, M13mp21IR62E DNA was digested with BamHI after treatment with T4 Endo VII-containing crude extracts. BamHI digestion alone, like digestion with wild-type T4 Endo VII, cleaves the M13mp21IR62E DNA once, converting circular substrate molecules into linear molecules of 7.2 kb. Subsequent BamHI digestion of M13mp21IR62E treated with T4 Endo VII results in the production of two restriction fragments of 4.0 kb and 3.2 kb. Thus, this assay measures the linearization of a cruciform-containing substrate by generating diagnostic restriction fragments following stepwise treatment with T4 Endo VII and a unique restriction enzyme.

In more detail, these experiments were performed as follows. A 10 μl reaction mixture containing 42 fmoles (200 ng) of supercoiled RFI-DNA of M13mp21IR62E, 1 μl of T4 Endo VII 10X reaction buffer (500 mM Tris/HCl (pH 8.0), 100 mM Mgcl$_2$, 100 mM ME), and 0.5 μg/μl BSA was prepared as described by Jensch et al. (*EMBO J.* 8:4325–4334, 1989). To this reaction mix was then added a crude lysate containing either wild-type T4 Endo VII or amE727-mutant T4 Endo VII at a dilution of either 1:1000 (FIG. 2, lanes 3 and 6) or 1:10,000 (FIG. 2, lanes 4, 5, 7, and 8), or previously purified T4 Endo VII prepared according to the method of Kosak et al. (*Eur. J. Biochem.* 194:779–784, 1990) (lane 9), and the mixture was incubated at 37° C. for 15 minutes.

Site-specific cleavage of RFI-DNA of M13mp21IR62E by T4 Endo VII was then monitored by digesting the T4 Endo VII-treated M13mp21IR62E with BamHI as follows. To the T4 Endo VII reaction mix, NaCl was added to a final concentration of 0.5M to inactivate T4 Endo VII. Next, 10U of BamHI were added, and the mixture was incubated for an additional 15 minutes at 37° C. The reaction mixture was then analyzed on a 1% agarose gel in TAC buffer (40 mM Tris/HOAc (pH 7.4), 5 mM sodium acetate, and 1 mM EDTA) containing 1 μg/ml ethidium bromide. Gels were photographed, and the two diagnostic restriction fragments of 4.0 kb and 3.2 kb were quantitiated by densitometer scanning.

Figure 2:
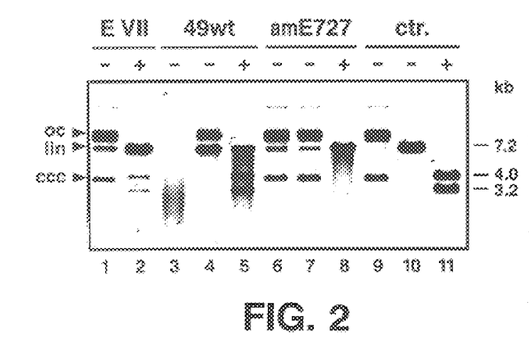
FIG. 2 is a photograph of a 1% agarose gel showing the activity of lysates prepared from BL21(DE3) cultures expressing recombinant wild-type or amE727-mutant T4 Endo VII resolvases. Dilutions of crude lysates were tested for T4 Endo VII site-specific cleavage activity using plasmid M13mp21IR62E which, under supercoiling conditions, carries a cruciform structure which acts as a substrate for T4 Endo VII. Lane 1, M13mp21IR62E treated with 0.2U T4 Endo VII; lane 2, M13mp21IR62E treated with 0.2U T4 Endo VII and BamHI; lane 3, M13mp21IR62E treated with crude lysate (diluted 1:1,000) containing wild-type T4 Endo VII; lane 4, M13mp21IR62E treated with crude lysate (diluted 1:10,000) containing wild-type T4 Endo VII; lane 5, M13mp21IR62E treated with crude lysate (diluted 1:10,000) containing wild-type T4 Endo VII; lane 6, M13mp21IR62E treated with crude lysate (diluted 1:1,000) containing amE727-mutant T4 Endo VII; lane 7, M13mp21IR62E treated with crude lysate (diluted 1:10,000) containing amE727-mutant T4 Endo VII; lane 8, M13mp21IR62E treated with crude lysate (diluted 1:10,000) containing amE727-mutant T4 Endo VII; lane 9, M13mp21IR62E substrate mock-treated with T4 Endo VII; lane 10, M13mp21IR62E linearized with EcoRI; and lane 11, M13mp21IR62E digested with EcoRI and BamHI. Locations for the three conformations of the M13mp21IR62E DNA substrates are marked on the left of the gel as nicked or open circle ("oc"), linearized circle ("lin"), and covalently closed circle with supercoil ("ccc"). Positions of the 7.0 kb, 4.0 kb, and 3.2 kb restriction fragments are shown on the right. Experiments using purified T4 Endo VII, crude lysates containing E. coli BL21(DE3)-derived wild-type T4 Endo VII, crude lysates containing E. coli BL21(DE3)-derived amE727-mutant T4 Endo VII, and control assays are designated at the top of the gel as "E VII," "48 wt," "amE727," and "ctr," respectively. The (-) or (+) signs shown above the lanes refer to the addition of BamHI.

The results shown in FIG. 2 demonstrate that crude lysate containing wild-type T4 Endo VII specifically cleaved supercoiled RFI-DNA from M13mp21IR62E at the cruciform structure. As shown in lane 4, plasmid M13mp21IR62E, when treated with wild-type T4 Endo VII-containing lysate, was linearized. Subsequent treatment with BamHI resulted in the production of restriction fragments of 4.0 and 3.2 kb, indicating that the wild-type enzyme cleaved specifically at the palindromic cruciform structure (FIG. 2, lane 5). Crude lysate containing the amE727-mutant T4 Endo VII, despite containing approximately 25 times more enzyme, exhibited only non-specific cleavage of the supercoiled cruciform RFI-DNA (FIG. 2, lane 8). As controls, 0.2U of T4 Endo VII (previously purified) was used to treat supercoiled cruciform RFI-DNA of the M13mp21IR62E plasmid substrate (FIG. 2, lanes 1 and 2), and the product was subsequently cut with BamHI (FIG. 2, lane 2). Also, as a control, the profile obtained from the mock-treatment of supercoiled cruciform RFI-DNA with T4 Endo VII is shown in FIG. 2, lane 9. And the restriction fragments from supercoiled cruciform RFI-DNA, either linearized with EcoRI or double digested with EcoRI and BamHI are shown in FIG. 2, lanes 10 and 11, respectively.

Overexpression and Purification of Wild-Type T4 Endo VII

To produce large quantities of T4 Endo VII, overexpression was carried out as follows. A single colony of BL21 (DE3) cells transformed with pRB210 was used to inoculate a 500 ml culture in LB/ampicillin (100 μg/ml) medium. This culture was grown overnight at 37° C., and then used to inoculate a fermenter containing 8 liters of LB/ampicillin (100 μg/ml) medium. Cells were grown at 30° C. under continuous stirring (600 rpm) and heavy aeration (5 liters/minute). At a cell density of approximately 5×10$^7$ cells/ml (OD$_{550}$=0.8), expression of T4 Endo VII was induced by the addition of IPTG to a final concentration of 1 mM. After 2 hours, cells were harvested by centrifugation and immediately frozen at −80° C. Thirty-five grams of cells were routinely obtained from one fermenter run. The cells could be stored without loss of activity for at least 6 months at −80° C.

To purify the enzyme, approximately 25 g of frozen cells were thawed in 100 ml of Buffer A [10 mM Tris/HCl, pH 8.0, 10 MM MgCl$_2$, 1 mM EDTA, 2 mM phenylmethylsufonylfluoride (PMSF), 10% glycerol (by volume), and 10 mM ME] and then sonicated for 30 minutes at a setting of 5 with a Branson sonifer equipped with a 0.5 cm tip. All purification steps were carried out at 4° C. or on ice, unless otherwise stated. To obtain a clear crude extract, insoluble cell debris was removed by centrifugation at 100,000×g for 45 minutes. More than 90% of the T4 Endo VII activity remained in the supernatant following centrifugation. An analysis of this fraction, termed Fraction I, is shown in Table I (below).

Nucleic acids were next removed from Fraction I by polyethylene glycol-dextran (PEG/Dex) two phase separation. To 100 ml of cleared crude extract, 30.2 ml of polyethyleneglycol (PEG) 6000 (from a 30% mass/vol. stock-solution) and 11.2 ml of dextran T500 (from a 20% mass/vol. stock-solution) (both in Buffer A) were added. Finely ground NaCl was then slowly added, with stirring, to a final concentration of 4M. The resulting suspension was stirred for an additional hour. Next, the PEG and dextran phases were separated by low speed centrifugation (30 minutes, 10,000×g) using a Sorvall SS34 rotor. The top phase, containing PEG and T4 Endo VII, was removed and dialyzed overnight against 8 liters of Buffer B (10 mM Tris/HCl, pH 8.0, 2 mM EDTA, 10 mM ME, and 10% glycerol (by vol.)) containing 300 mM KCl. After dialysis, the solution was again cleared by low speed centrifugation. The resulting supernatant was referred to as Fraction II and is described in Table I (below).

Figure 3A:
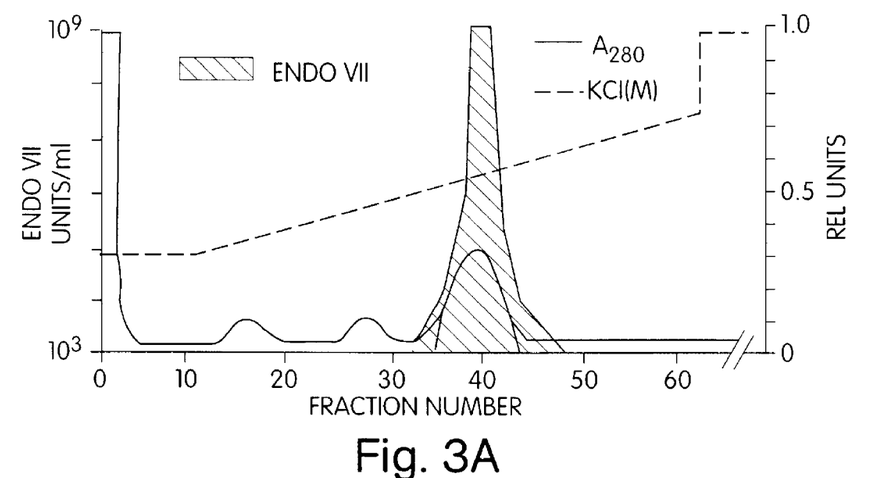
FIGS. 3A and 3B are chromatograms showing the elution profiles of recombinant wild-type T4 Endo VII prepared from E. coli strain BL21(DE3) on a heparin-agarose column (FIG. 3A) or on a Mono-Q column (FIG. 3B). The absorbency at 280 nm (—) was monitored continuously, and T4 Endo VII activity (denoted by the shaded background) was determined in fractions as described herein. The programmed linear KCl gradients from 300–700 mM and 50–1,000 mM KCl for both the heparin-agarose and Mono-Q columns, respectively, are indicated as ( . . . ).

Fraction II was then loaded onto a 40 ml heparin-agarose (Sigma Chemicals, Deisenhofen, Germany) column equilibrated with Buffer B containing 300 mM KCl. Chromatographic procedures were performed using FPLC equipment from Pharmacia (Freiburg, Germany). After loading, the column was washed with 4 bed volumes of the same buffer, and the protein was eluted with 5 bed volumes of a linear gradient of 300–700 mM KCl Buffer B at a flow rate of 1.5 ml/minute. Fractions (of 5 ml) were collected and evaluated for T4 Endo VII activity as described below. The elution profile is shown in FIG. 3A. T4 Endo VII activity was generally found in fractions having greater than 520 mM KCl. Fractions containing T4 Endo VII activity were then pooled and dialyzed overnight against 8 liters of Buffer B containing 50 mM KCl. The dialyzed pooled fractions of T4 Endo VII activity are referred to as Fraction III and shown in Table I (below).

Figure 3B:
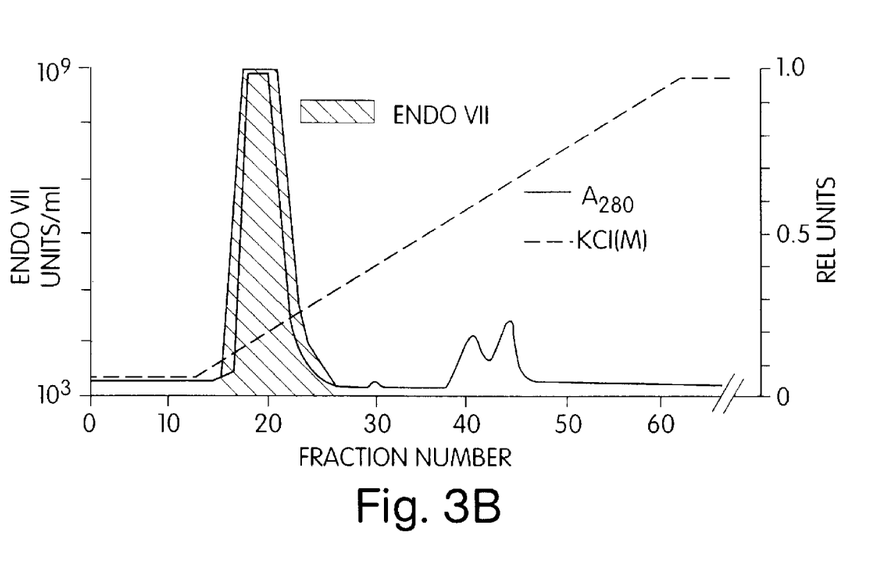
Figure 4A:
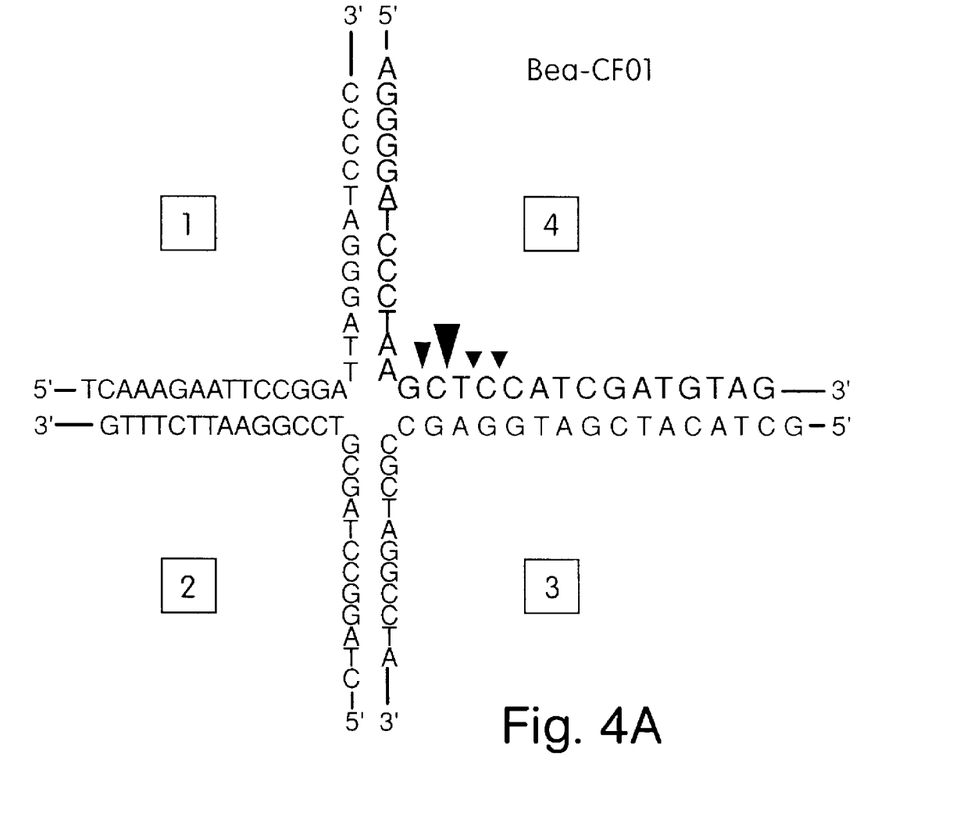
FIGS. 4A, 4B, 4C, and 4D are a set of schematic illustrations showing the conformations of the cruciform Bea-CF01 (FIG. 4A) (SEQ ID NOS: 3–6) and hairpin Bea-MMCC(H46) (FIG. 4C) (SEQ ID NO: 7) substrate oligonucleotides, as well as a set of photographs showing electrophoretic analysis of T4 Endo VII-induced fragments produced from digestion of cruciform Bea-CF01 (FIG. 4B) and hairpin Bea-MMCC(H46) (FIG. 4D) substrates with different concentrations of E. coli BL21(DE3)-purified T4 Endo VII.
Figure 4B:
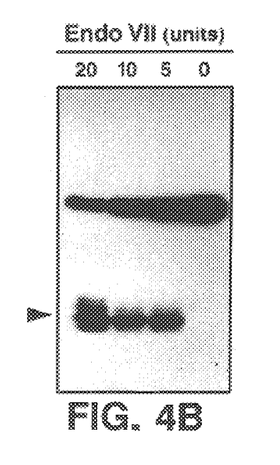
Figure 4C:
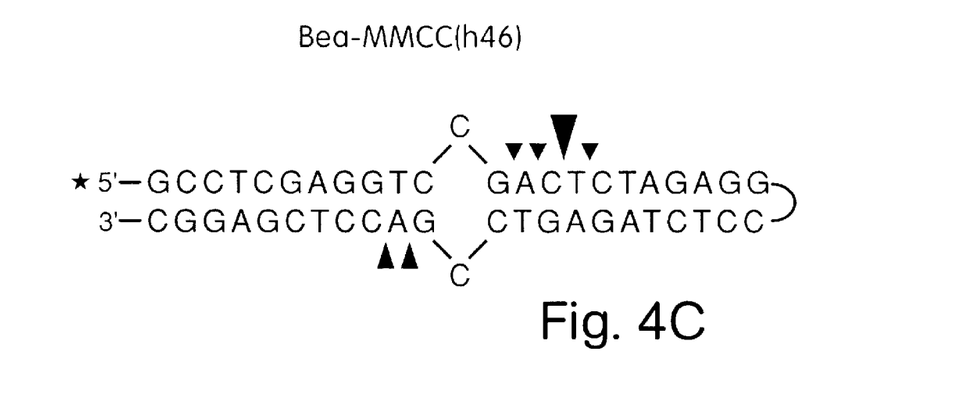
Figure 4D:
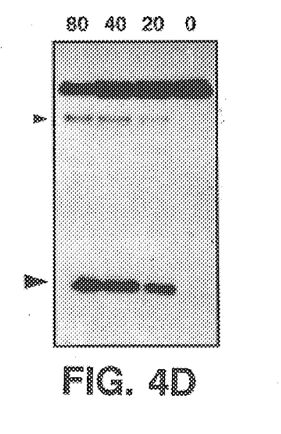

For further purification, Fraction III was loaded onto a Mono-Q FPLC column (HR 10/10, Pharmacia, Piscataway, N.J.) equilibrated with Buffer B containing 50 mM KCl. After loading, the column was washed with 4 bed volumes of Buffer B containing 50 mM KCl, and the protein was eluted with 8 bed volumes of a linear gradient of 50–1000 mM KCl in Buffer B at a flow rate of 0.8 ml/minute. Fractions (of 1 ml) were collected and evaluated for T4 Endo VII activity as described below. The elution profile is shown in FIG. 3B. The majority of the T4 Endo VII activity generally appeared in the range of 150 mM to 250 mM KCl. Fractions having T4 Endo VII activity were pooled and stored in 50% glycerol at −20° C. This is referred to as Fraction IV and is shown in Table I (below).

In all purification steps, protein fractions were assayed for T4 Endo VII activity using the VFS-DNA assay described by Kosak et al. (*Eur. J. Biochem.* 194:779–784, 1990). This method involves labelling VFS-DNA with tritium and assaying its degradation by T4 Endo VII. For this assay, T4 Endo VII was diluted in ice-cold Buffer D (i.e., 10 mM Tris/HCl (pH 7.5), 0.1 mM glutathione, and 50% glycerol (by vol.)). A standard reaction contained, in a 100 μl total volume, 10 μl of T4 Endo VII reaction buffer (10X), 25 μg BSA, and 150 ng of tritium-labeled very fast-sedimenting DNA ($[^3H]$-VFS-DNA). $[^3H]$-VFS-DNA was purified from phage amE727-infected *E. coli* cells as previously described by Kemper et al. (*J. Virol.* 18:1000–1015, 1976; *Eur. J. Biochem.* 115:123–131, 1981). After the addition of sample containing T4 Endo VII, the mixture was incubated for 15 minutes at 37° C. The reaction was stopped by addition of 900 μl of ice-cold T4 Endo VII stop buffer (50 mM Tris/HCl (pH 8.0), 100 mM EDTA, and 0.2% sarcosyl (by vol.)), and the the reaction mixture centrifuged for 30 minutes at 17,500 rpm in a Sorvall SM24 rotor. The top phase (200 μl) was recovered, and its content of radioactivity was determined according to standard procedures. An increase in radioactivity in the supernatant reflected the degradation of VFS-DNA; undegraded $[^3H]$-VFS-DNA was pelleted. One unit of T4 Endo VII activity was defined as that amount of enzyme which converted 50% of the VFS-DNA into products of low molecular weight.

Figure 5:
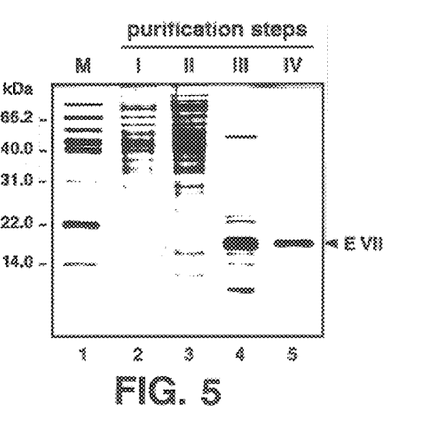

Active fractions from each stage of purification were pooled and analyzed by SDS-PAGE according to the methods described herein. Protein was measured using the method of Bradford (*Anal. Biochem.* 72:248–254, 1976), a kit from BioRad, and BSA as a standard. FIG. 5 illustrates the reducing SDS-PAGE analysis of the purified T4 Endo VII fractions. After silver-staining, only a single polypeptide of approximately 18 kD was observed in the Mono-Q Fraction IV (FIG. 5).

Using the above expression system and the accompanying purification methods, the production of milligram amounts of pure recombinant T4 Endo VII were obtained, typically in about five days. In general, 25 grams of frozen IPTG-induced BL21(DE3) cells routinely provided at least 10 mg (typically, 13 mg) of recombinant T4 Endo VII protein, having a purity greater than 99.99% as determined on silver-stained gels. The specific activity of purified T4 Endo VII, as determined using the $[^3H]$-VFS-DNA assay, was typically $2.5 \times 10^8$ units/mg protein. This represented a 500-fold increase in protein production over an earlier described purification protocol (Kosak et al., *Eur. J. Biochem.* 194:779–784, 1990). Due to this increase in protein production, the enzyme required only a 45-fold purification, easily accomplished in two column chromatography steps. In addition, the decreased manipulations involved in this purification left the enzyme much more active.

Table I (below) shows the purification data for wild-type T4 Endo VII prepared from IPTG-induced BL21(DE3) cells expressing pRB210. Units of T4 Endo VII and milligrams of protein are expressed as total amounts recovered from each purification step. Yield refers to the percentage of units present after each purification step, and purification refers to the X-fold enrichment of activity per milligram of total protein as compared to the initial purification step.

TABLE I

Purification of T4 Endo VII

| Fraction | Step | Volume (ml) | Activity (units) | Protein (mg) | Yield (%) | Purification (-fold) |
|---|---|---|---|---|---|---|
| I | crude extract | 123 | $8.5 \times 10^9$ | 1630 | 100 | 1 |
| II | PEG/Dex | 260 | $7.5 \times 10^9$ | 1450 | 88 | 1 |
| III | Heparin-agarose | 80 | $4.2 \times 10^9$ | 38 | 49 | 21 |
| IV | Mono-Q | 7 | $2.8 \times 10^9$ | 13 | 33 | 45 |

Sensitivity of Different DNA Substrates to T4 Endo VII

The efficiency of overexpressed T4 Endo VII cleavage activity on $[^3H]$-VFS-DNA, supercoiled M13mp21IR62E, Bea-CF01, and Bea-MMCC(H46) substrates was also evaluated using the standard methods described herein. Efficiency of T4 Endo VII cleavage activity was monitored by determining the amount of T4 Endo VII required to degrade 50% of each of these substrates under assay conditions (described herein) that were standardized to both the amount of enzyme and to the number of potential cleavage sites in each substrate. The activity of T4 Endo VII on substrates Bea-CF01, Bea-MMCC(H46), and M13mp21IR62E can be compared directly because both the reaction conditions and molar substrate amounts were equivalent.

When M13mp21IR62E was used as a hairpin substrate for assaying T4 Endo VII cleavage activity, assays were carried out as described above. When synthetic oligonucleotides BeaCF01 or Bea-MMCC(H46) were used as substrates, the reactions were performed in 10 μl of T4 Endo VII reaction buffer (1X) containing 0.5 μg/μl BSA and 2 fmoles of oligonucleotide. The sequences of the mismatch-containing heteroduplex Bea-MMCC(H46) (SEQ ID NOS: 3, 4, 5, 6) and the cruciform DNA Bea-CF01 (SEQ ID NO: 7) are shown in FIG. 4. Following addition of purified recombinant enzyme, reaction mixtures were incubated for 15 minutes at 37° C. The reaction mixtures were then analyzed by denaturing PAGE by quantitating the amount of degradation product using a phosphoimager (BAS1000, Fuji).

Table II summarizes the results of these experiments. As shown, T4 Endo-VII exhibited a wide range of reactivities with the different DNA substrates. One standard unit of T4 Endo VII was defined as that amount which degraded 50% of 150 ng of $[^3H]$-VFS-DNA (Kemper et al., *Eur. J. Biochem.* 115:123–131, 1981). With four potential cleavage sites per unit genome, the VFS-DNA substrate contained 5.6 fmoles of cleavage sites. In comparison, the assays with M13mp21IR62E, Bea-CF01, and Bea-MMCC(H46) contained 42, 2, and 2 fmoles of cleavage sites, respectively. As shown in Table II, these substrates were recognized by T4 Endo VII with ½, ⅟₁₅, and ⅟₆₀ the efficiency of VFS-DNA.

Unless otherwise noted, all chemicals used in the experiments described herein were p.a. grade and purchased from Sigma Chemicals (Deisenhofen, Germany).

TABLE II

| | DNA | | | |
|---|---|---|---|---|
| Substrate | Total amount (ng) | Molecules (fmoles) | Cleavage sites (fmoles) | Sensitivity[1] (units T4 Endo VII) |
| [$^3$H]-VFS-DNA | 150 | 1.4 | 5.6 | 1 |
| M13mp21IR62E | 200 | 42 | 42 | 2 |
| Bea-CF01 | 0.73 | 2 | 2 | 15 |
| Bea-MMCC(H46) | 0.3 | 2 | 2 | 60 |

[1]Units of T4 Endo VII required to degrade 50% of the respective substrate in the standard assay.

Other Embodiments

Other embodiments are within the following claims.

For example, as discussed above, other chemically-inducible and, if desired, fully repressed expression systems may be utilized for T4 Endo VII production. Examples of other expression systems that rely on induction by a chemical stimulus include, without limitation, the arabinose, galactose, and alkaline phosphatase systems. Other chemical stimuli include, without limitation, 3-indolylacetic acid and nalidixic acid. Expression systems other than the lac repressor system that are readily repressed prior to induction include, without limitation, the lambda promoters $P_L$ and $P_R$, the tryptophan promoter, and the chemotaxis promoter.

Moreover, the T4 Endo VII protein produced according to the overexpression methods of the invention may be recovered and purified using any standard method known to those skilled in the art. Methods for the purification and recovery of enzymes such as T4 Endo VII are described, for example, in Benson et al., *EMBO J.* 13:5764–5771, 1994; Barry et al., *J. Biol. Chem.* 269:33049–33062, 1994; Cazaux et al., *J. Biol. Chem.* 269:8246–8254, 1994; Chi et al., *J. Biol. Chem.* 269:29984–29992, 1994; and Dunderdale et al., *J. Biol. Chem.* 269:5187–5194, 1994. In general, the properties of T4 Endo VII that are exploited in separation and purification include size, charge, solubility, and possession of specific binding sites. As is known in the art, the aim of a purification procedure is to isolate a given enzyme, e.g., T4 Endo VII, with the maximum possible yield, based on the percentage recovered activity. In addition, the preparation should possess the maximum catalytic activity (that is, degradation or inactivation of the enzyme should be minimized), and the enzyme should be of the highest possible purity, recovered from most, if not all, contaminating substances that substantially interfere with enzyme activity. The catalytic activity of a T4 Endo VII preparation is determined by any suitable assay in which the rate of disappearance of substrate or the rate of appearance of product is determined under defined conditions of substrate concentration, temperature, pH, ion concentration, and the like, e.g., those described herein. Criteria used in assessing the purity of a T4 Endo VII preparation involve the application of standard analytical methods well known in the art.

While the purification strategy described herein utilizes heparin and Mono-Q chromotography steps, other equivalent column steps may be employed to recover and purify overexpressed T4 Endo VII. Alternative chromatography techniques for this purpose include, without limitation, DEAE-cellulose, DNA-agarose, and Mono-S chromatography techniques.

While the methods of the invention preferably result in the overexpression and recovery of soluble T4 Endo VII enzyme, the methods of the invention also include overexpression and recovery of insoluble T4 Endo VII, for example, as found in inclusion bodies (i.e., dense particles containing precipitated proteins formed in the recombinant host). Soluble T4 Endo VII is recovered from the insoluble form using methods well known to those skilled in the art, e.g., solubilization and renaturation of the insoluble product to obtain an active protein product.

Individuals skilled in the art will readily recognize that the compositions of the present invention may be assembled into a kit for the detection of mismatches, e.g., mismatches diagnostic or prognostic of human diseases (for example, cancer), or for perinatal screening for inherited diseases, or differential diagnosis of diseases not readily detectable by conventional tests (for example, Marfan's syndrome and the fragile X syndrome). In addition, the overexpressed T4 Endo VII of the invention may be utilized for the mismatch analysis of genetic alleles or polymorphisms (for example, for genetic mapping, tissue typing, or forensic or identification purposes), or for pathogen typing (for example, for HIV strain identification). Such mismatch assays are described, for example, in Cotton et al., U.S. Ser. No. 08/232,530; Kemper et al., in *Structure & Methods*, vol. 1: *Human Genome Initiative & DNA Recombination*, eds. Sarma and Sarma, Adenine Press, Schenectady, N.Y., 1990, pp. 215–229; Babon et al., *Nucl. Acids Res.* 23:5082–5084, 1995; Solaro et al., *J. Mol. Biol.* 230:868–877, 1993; Youil et al., *Proc. Natl. Acad. Sci. USA* 92:87–91, 1995; Pottmeyer and Kemper, *J. Mol. Biol.* 223:607–615, 1992; and Birkenkamp and Kemper, *DNA Res.* 2:9–14, 1995, all hereby incorporated by reference.

Typically, kits will include at least T4 Endo VII enzyme produced according to the methods of the invention. optionally, the kit will also include pre-formed heteroduplexes with which to standardize reaction conditions and/or appropriate buffers (for example, enzyme dilution buffers or enzyme reaction buffers).

What is claimed is:

1. A method for the production of recombinant bacteriophage T4 endonuclease VII (T4 Endo VII), said method comprising:
   (a) providing a host cell that comprises a nucleic acid encoding T4 Endo VII, wherein expression of said T4 Endo VII is inducible;
   (b) inducing expression of said T4 Endo VII by applying a chemical stimulus; and
   (c) recovering said inducibly expressed T4 Endo VII from said host cell.

2. The method of claim 1, wherein said host cell is a prokaryotic cell.

3. The method of claim 2, wherein said prokaryotic cell is *E. coli*.

4. The method of claim 3, wherein said prokaryotic cell is *E. coli* BL21(DE3).

5. The method of claim 1, wherein said expression of said T4 Endo VII is fully repressed prior to induction.

6. The method of claim 1, wherein said expression of said T4 Endo VII is repressed by the lac repressor prior to induction.

7. The method of claim 1, wherein expression of said T4 Endo VII is under the control of a T7 promoter.

8. The method of claim 1, wherein said T4 Endo VII is inducibly transcribed by T7 RNA polymerase.

9. The method of claim 1, wherein said chemical stimulus is IPTG.

10. The method of claim 1, wherein said nucleic acid encoding T4 Endo VII is contained within the pET-11a vector.

11. The method of claim 1, wherein said T4 Endo VII is recovered in a soluble form.

12. The method of claim 1, wherein said recovery of said inducibly expressed T4 Endo VII includes heparin chromatography.

13. The method of claim 1, wherein said recovery of said inducibly expressed T4 Endo VII includes Mono-Q chromotography.

14. The method of claim 1, wherein said recovery of said inducibly expressed T4 Endo VII involves only two column chromatography steps.

15. The method of claim 1, wherein said T4 Endo VII is produced in quantities of at least 0.4 mg/kg of host cells.

16. The method of claim 15, wherein said T4 Endo VII is produced in quantities of at least 0.5 mg/kg of host cells.

17. The method of claim 1, wherein said recovered T4 Endo VII is at least 90% pure.

18. The method of claim 17, wherein said recovered T4 Endo VII is at least 99% pure.

19. The method of claim 1, wherein said recovered T4 Endo VII has a specific activity of at least $2.5 \times 10^8$ U/mg protein.

* * * * *

UNITED STATES PATENT AND TRADEMARK OFFICE
CERTIFICATE OF CORRECTION

PATENT NO. : 5,824,530
DATED : October 20, 1998
INVENTOR(S) : Börries Kemper, Stefan Golz, and Rainer P. Birkenbihl It is certified that error appears in the above-indentified patent and that said Letters Patent is hereby corrected as shown below:

ON THE TITLE PAGE:
Item [56]

In Other Publications, col. 2, line 13, replace "Bichem" with --Biochem--;

At col. 3, line 1, delete "and recovering milligram quantities of T4 Endo VII. By";

At col. 4, line 25, "(...)" with --(----)--;

At col. 5, line 31, replace
"GGGCTCGAGGCCTTAATGTTATTGACTGGCAAATTATAC" with
--GGGCTCGAGGCCTTAATGTTATTGACTGGCAAATTATAC--;

At col. 5, line 34, replace "ATGAATTAAGATCTCAATTTCTTTTTCAATTGTCA" with --ATGAATTAAGATCTCAATTTCTTTTTCAATTGTCA--;

At col. 7, line 22, replace "Mgcl$_2$" with --MgCl$_2$--;

At col. 8, line 20, replace "MM" with --mM--;

UNITED STATES PATENT AND TRADEMARK OFFICE
CERTIFICATE OF CORRECTION

PATENT NO. : 5,824,530
DATED : October 20, 1998
INVENTOR(S) : Borries Kemper, Stefan Golz, and Rainer P. Birkenbihl

It is certified that error appears in the above-indentified patent and that said Letters Patent is hereby corrected as shown below:

At col. 9, line 31, delete the first occurrence of "the".

Signed and Sealed this

Sixth Day of March, 2001

Attest:

NICHOLAS P. GODICI

Attesting Officer

Acting Director of the United States Patent and Trademark Office